(12) United States Patent
Schulman et al.

(10) Patent No.: US 7,908,014 B2
(45) Date of Patent: Mar. 15, 2011

(54) ANTENNA ON CERAMIC CASE

(75) Inventors: Joseph H. Schulman, Santa Clarita, CA (US); Howard H. Stover, Pasadena, CA (US); Brian J. Lasater, Wenatchee, WA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 1166 days.

(21) Appl. No.: 11/381,979

(22) Filed: May 5, 2006

(65) Prior Publication Data

US 2007/0260294 A1 Nov. 8, 2007

(51) Int. Cl.
*A61N 1/00* (2006.01)

(52) U.S. Cl. .......................................... 607/61

(58) Field of Classification Search ............... 607/2, 32, 607/30, 33, 60, 61, 115, 156
See application file for complete search history.

(56) References Cited

U.S. PATENT DOCUMENTS

| | | | |
|---|---|---|---|
| 2,771,561 A | 11/1956 | Fuller et al. | |
| 4,248,237 A * | 2/1981 | Kenny | 607/36 |
| 4,524,774 A | 6/1985 | Hildebrandt | |
| 5,058,581 A * | 10/1991 | Silvian | 607/32 |
| 5,245,745 A | 9/1993 | Jensen et al. | |
| 5,324,316 A | 6/1994 | Schulman et al. | |
| 5,391,199 A * | 2/1995 | Ben-Haim | 607/122 |
| 5,611,347 A * | 3/1997 | Davidson | 600/510 |
| 5,970,398 A | 10/1999 | Tuttle | |
| 6,122,494 A | 9/2000 | Tuttle | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,214,032 B1 | 4/2001 | Loeb et al. | |
| 6,765,779 B2 * | 7/2004 | Stevenson et al. | 361/302 |
| 6,804,561 B2 | 10/2004 | Stover | |
| 7,262,737 B2 * | 8/2007 | Zarnowitz et al. | 343/702 |
| 2002/0095195 A1 * | 7/2002 | Mass et al. | 607/60 |
| 2003/0023175 A1 * | 1/2003 | Arzbaecher et al. | 600/509 |
| 2005/0131509 A1 * | 6/2005 | Atanassoska et al. | 607/122 |
| 2006/0161225 A1 * | 7/2006 | Sormann et al. | 607/61 |

* cited by examiner

*Primary Examiner* — George Manuel
*Assistant Examiner* — Shubatra Narayanaswamy
(74) *Attorney, Agent, or Firm* — Gary D. Schnittgrund

(57) ABSTRACT

The invention is an antenna for use with an implantable microdevice, such as a microstimulator or microsensor, having a dipole antenna that is formed by ceramic processes on the inner or outer surface of the ceramic case of the microdevice. The antenna receives data transmitted from an external device, and transmits data to an external device. A dipole antenna may be formed from two radiating elements separated by an insulating material. A tuning circuit comprising capacitors and/or inductors is used to obtain resonance in the dipole antenna. In a preferred embodiment, the antenna is formed of a biocompatible material by applying a metal-containing paste to the ceramic case of the microdevice and thermally processing it.

11 Claims, 1 Drawing Sheet

ANTENNA ON CERAMIC CASE

FIELD OF THE INVENTION

This invention relates to an antenna and method to produce an antenna on a ceramic case of a microstimulator or microsensor that is injectable in living tissue.

BACKGROUND OF THE INVENTION

The present invention relates to an antenna on implantable medical devices that are suitable for placement in living tissue, and more particularly to small implantable stimulators or sensors, hereafter referred to as microstimulators or microsensors. Such medical devices have electrodes in contact with muscle or nerve fibers, through which the devices electrically stimulate the muscle or nerve fibers, or sense one or more physiological states present in the muscle or nerve fibers. More particularly, the invention relates to an antenna for such implantable microdevices, for both receiving signals from an external device, and transmitting signals to an external device.

It is desired to create a conductive metal line or coating on the small implantable stimulators or sensors that will perform as an antenna. Formation of an electrically conductive metal line on a glass or ceramic body is well known to one skilled in the art. Ceramic literature is replete with examples of metal formation on ceramic or glass where a slurry containing metal powder is applied by painting, silk screening, dipping, brushing the slurry on the ceramic and heat-treating it in traditional methods to leave an electrically conductive line or pattern of lines on the glass or ceramic. Every day examples include electrically heated backlights in automobiles for defogging the rear window when a switch is engaged.

It is also known in the ceramics art to form an antenna in glass or ceramic by placing a metallic conductor, such as a wire, on or within the ceramic body. One well-known example of such an antenna also comes from the automobile arena, where placing a wire between the glass layers of the laminated windshield forms a radio antenna for reception of AM or FM stations.

The need for small implantable stimulators or sensors that transmit or receive signals by means of an antenna arises from a variety of neuromuscular needs, such as neurological disorders that are often caused by neural impulses failing to reach their natural destination in otherwise functional body systems. Local nerves and muscles may function, but, for various reasons, injury, stroke, or other cause, the stimulating signals do not reach their natural destination.

For example, paraplegics and quadriplegics have intact muscles but lack the complete brain-to-muscle nerve link that conducts the signal to the muscles.

Prosthetic devices have been used for some time to provide electrical stimulation to excite muscle, nerve or other cells to provide relief from paralysis, and various other physical disorders have been identified which may be treated by electrical stimulation devices. Some of these devices have been large bulky systems providing electrical pulses through conductors extending through the skin. Disadvantageously, complications, including the possibility of infection, arise in the use of stimulators that have conductors extending through the skin.

Other smaller stimulators have been developed that are fully implantable and that are controlled through high frequency, modulated RF, telemetry signals. Such systems designed to stimulate nerves or muscles to provide motion are know as Functional Electrical Stimulation (FES) systems. An FES system using telemetry signals is set forth in U.S. Pat. No. 4,524,774 for "Apparatus and Method for the Stimulation of a Human Muscle." The '774 patent teaches a source of electrical energy, modulated in accordance with desired control information, to selectively power and control numerous, small stimulators, disposed at various locations within the body. Thus, for example, a desired progressive muscular motion may be achieved through the successive or simultaneous stimulation of numerous stimulators, directed by a single source of information and energy outside the body.

Many difficulties arise in designing implanted stimulators that are small in size, and in passing sufficient energy and control information to the stimulators to satisfactorily operate them without direct connection. A design of a small functionally suitable stimulator, a microstimulator, is taught is U.S. Pat. No. 5,324,316 for "Implantable Microstimulator." The '316 patent teaches all the elements required for successful construction and operation of a microstimulator. The microstimulator is capable of receiving and storing sufficient energy to provide the desired stimulating pulses, and is also able to respond to received control information defining pulse duration, current amplitude and shape. The microstimulator of the '316 patent is easily implanted, such as by injection by a hypodermic needle. The '316 patent is incorporated herein by reference.

Known microstimulators utilize a telemetry receiver based on modulating an inductive power signal provided to the microstimulator. Similarly, signals are transmitted from the microstimulator using the same circuits. By using components already present in the microstimulator, these telemetry systems do not require substantial additional circuitry. However, such inductive telemetry methods are limited by the resonant frequencies of the existing coil, which are typically below 2 MHz. While this approach has proven adequate for many applications, there are potential problems with interfering signals. Further, much higher frequencies, 402 to 405 MHz, have been designated by the Federal Communications Commission (FCC) for use with medical devices.

Telemetry methods utilizing monopole and dipole antennas are known for use in the FCC designated frequency range, however, such antennas are, primarily, electrical field devices. Electrical field devices suffer from high tissue detuning (i.e., the surrounding tissue interacts with the electrical nature of circuit components to the extent that some effectiveness of tuning is lost) and may not provide the best performance for implantable devices. Other telemetry systems utilizing a loop antenna inside the microdevice are also known in the art, see U.S. Pat. No. 6,804,561 B2, for example. Loop antennas have the advantage of being magnetic field devices, and are therefore less susceptible to tissue detuning. However, placing the loop antenna inside the case of a microdevice exhausts scarce space within the microdevices.

A need exists for a telemetry system that does not suffer from high tissue detuning loss, that does not take up substantial space inside the implantable microdevice, and that is suitable for operation in the 402 to 405 MHz frequency range.

SUMMARY OF THE INVENTION

The apparatus of the instant invention addresses the above and other needs by providing a dipole antenna formed on the case of an implantable microdevice.

The antenna receives data transmitted from an external device, and transmits data to an external device. Such a dipole antenna may be formed from two cylindrical sections separated by an insulating material on the case of the microdevice, or by separating a metal cylinder into two parallel semi-cylinders separated by an insulating material. A tuning circuit comprising capacitors and/or inductors is used to obtain resonance in the dipole antenna, thus creating a sufficiently large effective antenna impedance.

Advantageously, such a dipole antenna is suitable for operation in the 402 to 405 MHz frequency range.

In accordance with one aspect of the invention, a dipole antenna is formed on the case of an implantable microdevice. By forming the antenna on the case, space inside the microdevice is available for circuit components. In one embodiment of the invention, the existing electrodes, on the case of a microstimulator, are combined with a reactive circuit to create a dipole antenna.

In accordance with another aspect of the invention, a dipole antenna provided in an implantable medical device may be tuned with an array of capacitors and/or inductors. Because of the small physical size of the antenna, the antenna is not an effective radiator at the targeted operating frequencies without tuning. Accordingly, the reactance provided by an array of capacitors and/or inductors is adjusted to be equal to the inductive reactance of the dipole, resulting in a higher Q circuit and a larger effective antenna size.

In accordance with yet another aspect of the invention, a telemetry system using a dipole antenna provides non-inductive telemetry capability. Inductive telemetry requires that the transmitter and receiver be in very close proximity for effective operation. The telemetry system provided by the dipole antenna does not include such limitations.

The novel features of the invention are set forth with particularity in the appended claims. The invention will be best understood from the following description when read in conjunction with the accompanying drawings.

OBJECTS OF THE INVENTION

It is an object of the invention to form an antenna on the inner or outer surface of an implantable microdevice glass or ceramic case using an electrically conductive paste that is applied by ceramic processes.

Other objects, advantages and novel features of the present invention will become apparent from the following detailed description of the invention when considered in conjunction with the accompanying drawing.

DETAILED DESCRIPTION OF THE PREFERRED EMBODIMENT

Figure 1:
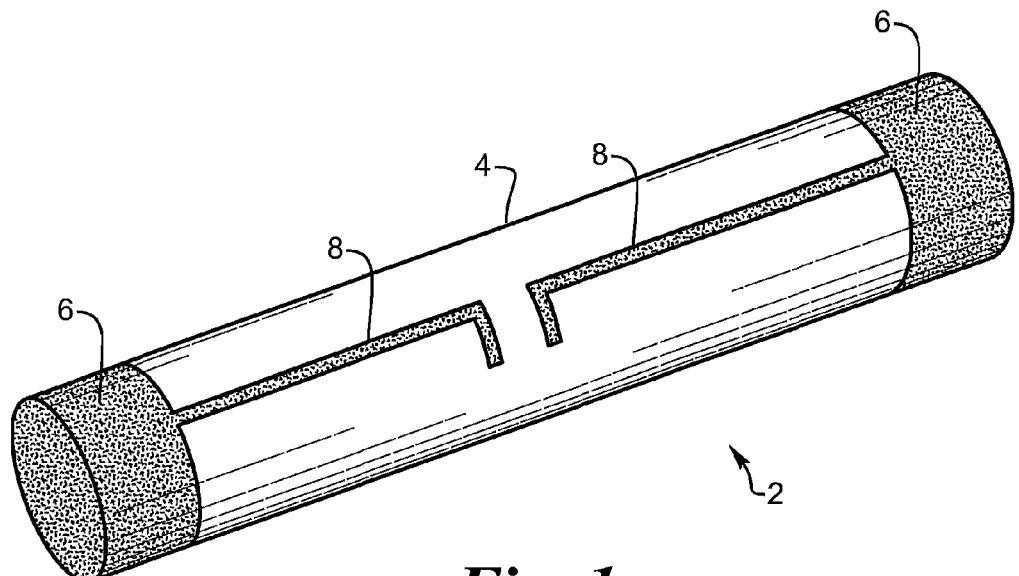
FIG. 1 illustrates a perspective view of the antenna assembly showing the implantable microsensor or microstimulator with an electrically conductive antenna formed on the outside of the ceramic case in a straight line pattern.

FIG. 1 provides a perspective view of a preferred embodiment of the antenna 8 that has been formed on the outside surface of the ceramic case 4 of the implantable device 2.

Typical dimensions for this device are about 5 to 60 mm in length and about 1 to 6 mm in diameter. (See, for example, U.S. Pat. Nos. 6,164,284, 6,185,452 and 6,208,894 which are incorporated herein by reference in their entirety.) Microstimulators, as exemplified by the BION® microstimulator manufactured by the Advanced Bionics Corporation of Santa Clarita, Calif., are typically elongated devices with metallic electrodes at each end that deliver electrical current to the immediately surrounding living tissues. While element 2 is generally described as an implantable stimulator, it is recognized that the present invention is equally applicable when element 2 is operable as a sensor or as both a stimulator and a sensor. Implantable device 2 includes insulating case 4, which typically is hollow and contains an electronics package and a power source, such as a battery, capacitor, a magnetic field coupled electrical energy generator, and electrically conductive case ends 6, each of which has an electrically conductive electrode which conducts electrical signals from a stimulator and/or to a sensor, depending upon the design and function of that particular miniature stimulator 2. Stimulator 2 may have at least one electrode, e.g., 2-8 or more, depending upon its particular design and function, although, for illustrative purposes, only two electrodes are shown in FIG. 1.

Insulating case 4 contains the electronics, which may include a battery or other energy storage device and signal generating or receiving circuitry and is made of an electrically insulating material that is capable of being hermetically sealed and that is also biocompatible, such as glass or ceramic. The ceramic may be alumina, glass, titania, zirconia, stabilized-zirconia, partially-stabilized zirconia, tetragonal zirconia, magnesia-stabilized zirconia, ceria-stabilized zirconia, yttria-stabilized zirconia, or calcia-stabilized zirconia, and in a preferred embodiment, insulating case 4 is yttria-stabilized zirconia, although other insulating materials may also be used. The insulating case 4 must be a material that is biocompatible as well as capable of being hermetically sealed, to prevent permeation of bodily fluids into the case.

The electrically conductive case end 6 is preferably a biocompatible, non-corrosive material, such as titanium or a titanium alloy, although other metals such as platinum, iridium, platinum-iridium, stainless steel, tantalum, niobium, or zirconium may be used. The preferred material is Ti-6AI-4V. An alternate preferred material is platinum-iridium.

The straight line dipole antenna 8 is preferably formed on the ceramic case by applying a thick film metallization layer to the ceramic by brushing, although silk screening, spraying, or dipping and other known techniques may alternatively be employed. A preferred material is platinum, which is preferably applied as a fritless ink having a solids content of about 85%, a preferred source being Heraeus OS2 fritless platinum ink. It is applied at room temperature and spatulated well before application to the ceramic surface. After application, it is preferably dried at 90° to 130° C. in air until it no longer is losing weight, typically about 10 minutes, which indicates that the organic termineol, or other thinner, has been evaporated. The ceramic case 4 and antenna 8 are fired at 900° to 1200° C. for 10 to 30 minutes at temperature in vacuum, although in an alternate approach the firing atmosphere may be air. The fired metal antenna 8 of platinum has resistivity of less than 40 milliohms per square at 10 micrometers fired film thickness.

The antenna 8 may be comprised of other materials, such as platinum, silver, gold, palladium or mixtures of these materials. It is desirable that biocompatible metals, such as platinum, silver, or gold be selected, although it is possible to apply a protective coating over the antenna 8 in order to hermetically seal it from direct exposure to living tissue.

Figure 2:
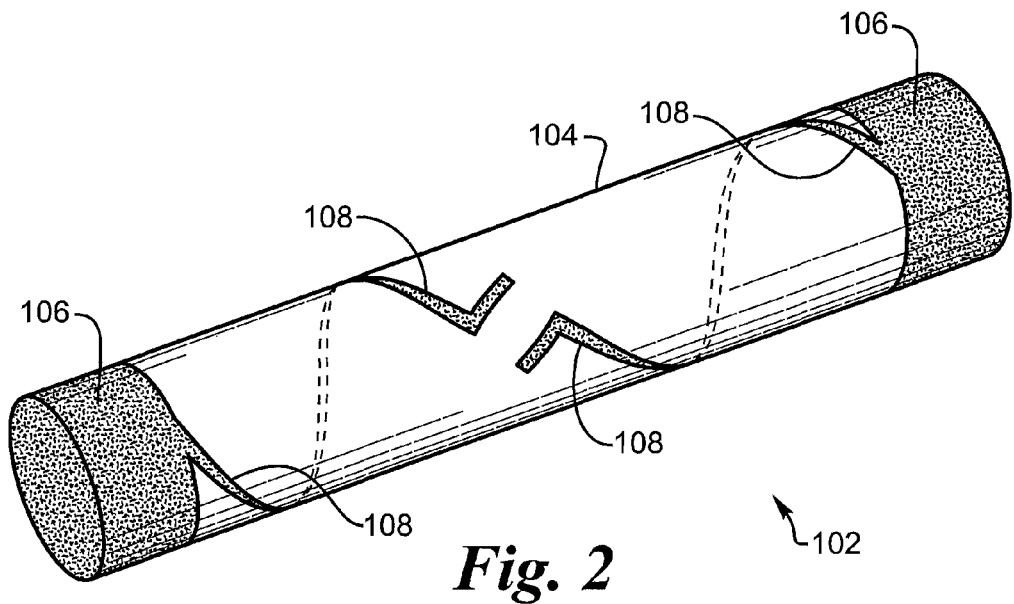
FIG. 2 illustrates a perspective view of the antenna assembly showing the implantable microsensor or microstimulator with an electrically conductive antenna formed on the outside of the ceramic case in a serpentine pattern.

FIG. 2 provides a perspective view of an alternative embodiment of the antenna 8 that has been formed on the outside surface of the ceramic case 4 of the implantable device 102. It is to be understood that the antenna 108 may be formed on the inside of the ceramic case 104. In this embodiment, implantable device 102 includes insulating case 104, which typically is hollow and contains an electronics package and a power source, such as a battery, capacitor, magnetic filed coupled electrical energy generator, and electrically conductive case ends 6, each of which has an electrically conductive electrode which conducts electrical signals from a stimulator and/or to a sensor, depending upon the design and function of that particular miniature stimulator 102.

As seen in FIG. 1, the present invention applies to a microdevice 2 implanted in a patient 10. An external device transmits signals to the microdevice 2 and the microdevice 2 transmits signals to the external device 14. The signals 18 transmitted to the microdevice 12 are principally control signals. The signals 16 transmitted from the microdevice 12 may be status signals, including diagnostic signals and/or performance signals (e.g., battery voltage), or signals that represent sensed physiological values.

The present invention pertains to a dipole antenna 8 formed on the case of the microdevice 12. Such a dipole antenna 13 is shown in FIGS. 1 and 2 in the form of electrically conductive lines 8 and 108, respectively. The antenna 8 and 108 are preferably separated into two segments by a gap or in an alternative embodiment by an insulating material.

The dipole antenna, when immersed in a conductive medium, such as living tissue, tends to form a loop antenna with the dipole antenna elements forming a portion of the loop and the path through the conductive medium forming another portion of the loop. Formation of an effective loop antenna exhibits less sensitivity to the proximity of additional body elements than one would expect to experience with a dipole antenna, and in fact it behaves in a manner similar to a loop antenna as used for paging devices and other electronic devices often held close to the body.

A tuning element is typically required to tune a dipole antenna. The tuning element is reactively matched to the radiating element to create a resonant circuit. It is well known in the art to tune the circuit by utilizing inductors to lengthen the antenna or capacitors to shorten the antenna.

The embodiments described in FIGS. 1 and 2 are intended for use with a microdevice having a cylindrical case. Such a cylindrical microdevice is well suited for implanting using a large gauge needle or a cannula, as disclosed in U.S. Pat. No. 6,214,032, which is incorporated in its entirety by reference herein.

However, those skilled in the art will recognize that many other shapes are viable for implantable microdevices. While the cylindrical and semi-cylindrical radiating elements of FIGS. 1 and 2 may not be appropriate for a non-cylindrical microdevice, the concepts taught for a cylindrical microdevice are readily adaptable to other shapes, and fall within the scope of the present invention.

Other electrode arrangements will be apparent to those skilled in the art. Many of these arrangements may be modified to provide a radiating element for a dipole antenna, and such arrangements are intended to fall within the scope of the present invention.

Obviously, many modifications and variations of the present invention are possible in light of the above teachings. It is therefore to be understood that, within the scope of the appended claims, the invention may be practiced otherwise than as specifically described.

What is claimed is:

1. A dipole antenna formed on an implantable microdevice, said implantable microdevice having a case, said case being a hollow cylinder having an inner and an outer surface and adapted for housing communications circuitry, said dipole antenna comprising:
   at least two radiating elements, wherein said radiating elements are electrically conducting and are formed of a thick film layer on said outer surface;
   wherein said dipole antenna is electrically coupled to said communications circuitry to create a telemetry system for said implantable microdevice; and
   wherein said case is comprised of a ceramic from the group consisting of alumina, glass, titania, zirconia, stabilized-zirconia, partially-stabilized zirconia, tetragonal zirconia, magnesia-stabilized zirconia, ceria-stabilized zirconia, calcia-stabilized zirconia, and yttria-stabilized zirconia.

2. The dipole antenna of claim 1, further comprising a tuning element that is electrically coupled to said radiating element, wherein said tuning element and said radiating element combine to form a resonant circuit.

3. The dipole antenna of claim 1, wherein said case is comprised of zirconia.

4. The dipole antenna of claim 1, wherein said radiating element is comprised of silver, platinum, palladium, or gold and no glass.

5. The dipole antenna of claim 1, wherein said radiating element is formed by brushing.

6. The dipole antenna of claim 1, wherein said implantable microdevice is a microstimulator.

7. The dipole antenna of claim 1, wherein said implantable microdevice is a microsensor.

8. The dipole antenna of claim 1, wherein said telemetry system receives a control signal from an external device.

9. The dipole antenna of claim 1, wherein said telemetry system transmits a signal to an external device.

10. The dipole antenna of claim 1, wherein said telemetry system has an operating frequency in the range of 402 to 405 MHz.

11. A dipole antenna formed on the outer surface of a case, comprising:
   a tuning element that is electrically coupled to a radiating element, wherein said tuning element and said radiating element combine to form a resonant circuit;
   at least two radiating elements, wherein said radiating elements are electrically conducting and are formed of a thick film layer on the outer surface of the case; and
   wherein said dipole antenna forms a loop antenna when immersed in electrically conductive living tissue; and
   wherein said case is comprised of a ceramic from the group consisting of alumina, glass, titania, zirconia, stabilized-zirconia, partially-stabilized zirconia, tetragonal zirconia, magnesia-stabilized zirconia, ceria-stabilized zirconia, calcia-stabilized zirconia, and yttria-stabilized zirconia.

* * * * *